United States Patent
Ulrich et al.

(10) Patent No.: US 6,542,234 B1
(45) Date of Patent: Apr. 1, 2003

(54) METHOD OF DETECTING THE PARTICLES OF A TOBACCO PARTICLE STREAM

(75) Inventors: Reinhard Ulrich, Buchholz (DE); Arno Weiss, Norderstedt (DE); Gerald Schmekel, Elmshorn (DE); Heinz-Werner Masurat, Neuenmarkt (DE); Uwe Werner Ehling, Goldkronach (DE)

(73) Assignee: British-American Tobacco (Germany) GmbH, Hamburg (DE)

( * ) Notice: Subject to any disclaimer, the term of this patent is extended or adjusted under 35 U.S.C. 154(b) by 173 days.

(21) Appl. No.: 09/680,012

(22) Filed: Oct. 5, 2000

(30) Foreign Application Priority Data

Oct. 8, 1999 (DE) .......................... 199 48 559

(51) Int. Cl.[7] .............................................. G01B 11/02
(52) U.S. Cl. ...................... 356/335; 356/627; 356/638; 250/559.21
(58) Field of Search ................... 356/335, 627, 356/634, 638, 639, 640; 250/559.21, 559.24

(56) References Cited

U.S. PATENT DOCUMENTS

| | | | | |
|---|---|---|---|---|
| 3,028,501 A | * | 4/1962 | Lamparter | ................... 356/627 |
| 3,591,290 A | * | 7/1971 | Zinner et al. | ................ 356/335 |
| 4,513,755 A | | 4/1985 | Baroni | |
| 4,835,605 A | | 5/1989 | Melchior et al. | |
| 4,903,374 A | | 2/1990 | Hosel | |
| 5,074,658 A | * | 12/1991 | Tavlarides et al. | .......... 356/627 |

FOREIGN PATENT DOCUMENTS

| | | |
|---|---|---|
| DE | 3216486 A1 | 11/1982 |
| DE | 2855583 C2 | 7/1984 |
| DE | 3706502 A1 | 9/1988 |
| DE | 3236261 C2 | 10/1991 |
| DE | 4119240 C2 | 3/1993 |
| DE | 4215908 A1 | 11/1993 |
| DE | 19706890 A1 | 10/1997 |
| DE | 43 07 407 C2 | 12/1998 |
| EP | 0 157 977 | 10/1985 |

* cited by examiner

*Primary Examiner*—Richard A. Rosenberger
(74) *Attorney, Agent, or Firm*—John F. Salazar; Middleton Reutlinger

(57) ABSTRACT

The invention relates to a method of detecting the particles of a tobacco particle stream in the production of smokable articles by scanning by means of a fine-beam light barrier, the diameter of which is smaller than the dimensions of the tobacco particles, and from the distribution of the dimensions of the tobacco particles determined by darkening of the fine-beam light barrier.

22 Claims, 6 Drawing Sheets

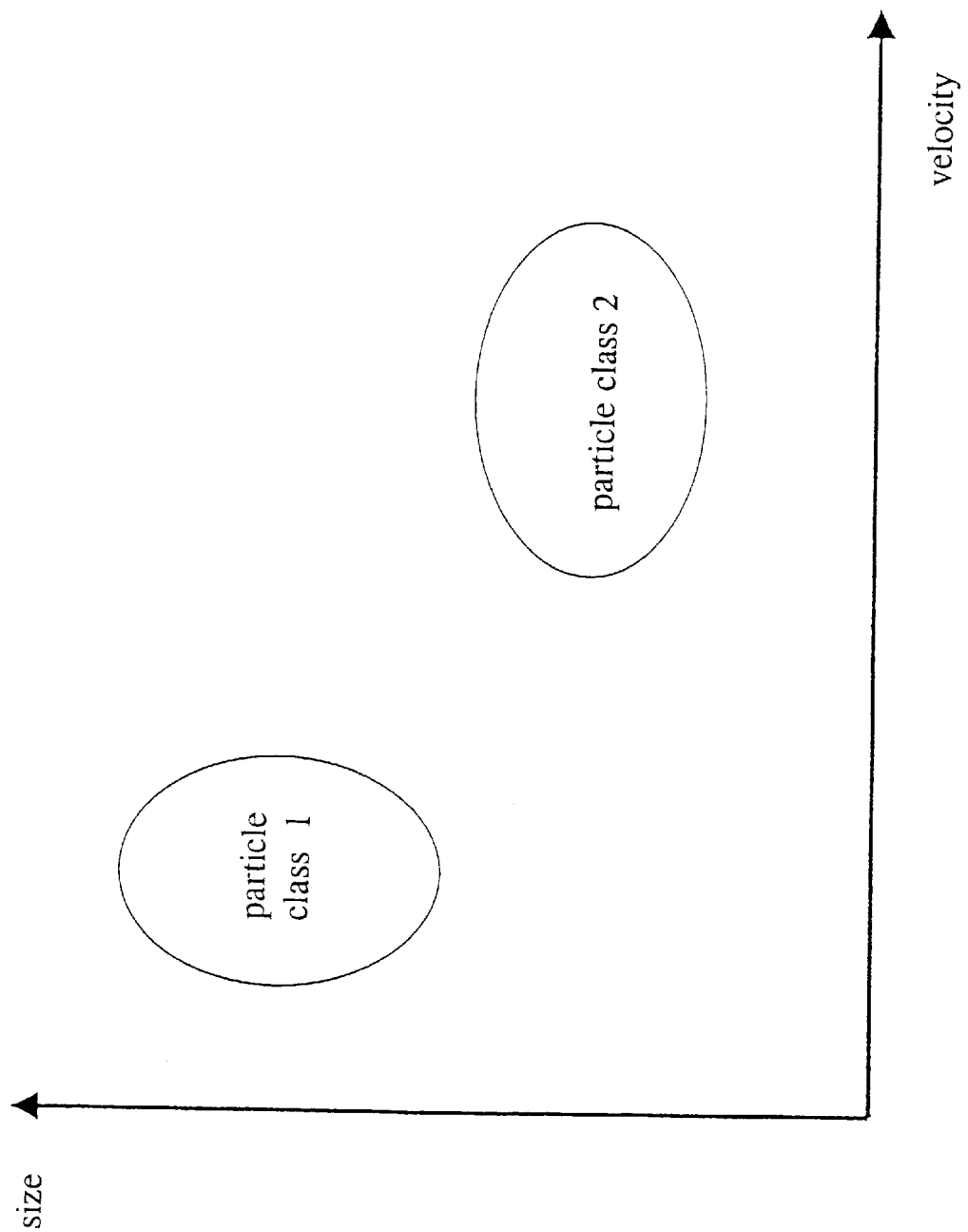

METHOD OF DETECTING THE PARTICLES OF A TOBACCO PARTICLE STREAM

BACKGROUND OF THE INVENTION

1. Technical Field

The invention relates to a method of detecting the particles of a tobacco particle stream in the production of smokable articles, in particular of winnowings.

In cigarette production, the incoming tobacco stream in the cigarette maker is screened. Only sufficiently fine material is incorporated in the bundle. The remaining portion of the more coarse material, the so-called "winnowings", is eliminated by the screening process and is collected centrally by pneumatic transport for further processing.

In order to optimize operation of the cigarette maker, it is important to determine online the mass stream of winnowings to and in operation of the cigarette maker as well as the size distribution of the winnowings, and to make use of the resulting parameters in adjusting separation of the winnowings. Up until now, detection of the winnowings was not effectuated at the cigarette maker, instead (if at all performed) it was carried out offline by sieve analysis of the eliminated winnowings. The ensuing measured results may then serve to optimize the screening conditions online as regards high product quality (elimination of practically all winnowings), i.e. by exclusively eliminating winnowings. However, optimization would be quicker and more flexible if analysis of the winnowings mass stream would be possible online directly at the winnowings exit of the cigarette maker. Measuring the mass stream in this way must take place at variable velocity of the transport air stream so that proper functioning is also assured given changing operation parameters of the cigarette maker, and the accuracy of the measured results should be independent of fluctuations in the particle size of the winnowings. In addition, it is of interest for continuous process monitoring to obtain information as to the momentary size distribution from the winnowings particle stream, for instance as regards the average particle size and the spread of the size distribution so as to be able to recognize quickly and selectively malfunctioning of the screening process.

This is, by definition, not possible with offline sieve analysis employed up to now.

2. Description of Related Art

In other technical fields outside of cigarette production, various optical screening methods have already been developed. Thus, patent DE 41 19 240 C2 discloses a method of determining the particle size distribution of a particle mixture in which the individual particles have a spherical shape. The particle mixture moves past an optoelectronic measuring length perpendicular to a parallel light beam and is optoelectronically scanned linewise. The chord lengths of the particles are measured and are assigned specific length classes by a classifier; from which the particle size distribution is computed in accordance to particle size classes defined according to the particle diameters of the corresponding length classes.

As the shapes of the winnowings greatly differ from spherical shapes, this method cannot be implemented for screening tobacco particles.

Patent DE 32 36 261 describes a method of determining the average radius and/or the average length of particles transported in a stream medium which fly through two slots of a mask. The beam emitted, dispersed or absorbed by the particles in passing through these slots is monitored to thus enable certain particles to be identified which have fully passed through both slots. This method is also not suitable for screening tobacco winnowings due to their irregular shapes.

A similar method is disclosed by patent DE 197 06 890 A, in which the particles are identified for which the emitted, dispersed or absorbed beam has a predefined relationship; the size of the identified particles is determined from the amount of emitted, dispersed or absorbed beams when the identified particles pass through the slots.

Patent DE 37 06 502 discloses a device for determining the grain distribution of a powdery product using two measuring cells which may be introduced in the beam path of a laser beam alternately so that one measuring cell is available for operation while, simultaneously, the second measuring cell is being cleaned.

Patent DE 42 15 908 A discloses an optical particle measuring method for clean room monitoring and for keeping a check on high-purity fluid, in which the particles directed through the measured volume are beamed and an imaging device, including a detector, detects the resulting diffused light; the radiation for the measured volume is modulated such that a measuring signal, modulated in time, materializes and renders possible improvement of the signal-to-noise ratio.

Patent DE 28 55 583 C2 describes a method for determining the grain distribution of grain mixtures which are statically recorded by means of a TV camera and the data is processed as a function of the statically projected images of the falling grains. Calibration measurements are made on a sieved-out grain class from the grain mixture, and under the assumption that the grains have the configuration of an ellipsoid of rotation, an average configuration coefficient is determined as the average value of the relationship of the longitudinal axis to the short axis of the grains. This shape assumption of an ellipsoid of rotation is likewise not applicable to tobacco particles.

Shown in patent 32 16 486 is a detector for the trimmed surplus tobacco in cigarette production. All of the trimmed surplus tobacco is pneumatically passed through the detector, the light beam of which is dimmed by the tobacco stream in a similar manner as a screen. The strength of the current generated by the photocells of the detector is thus inversely proportional to the density of the tobacco stream, and thus to the tobacco throughput. The detection of individual tobacco particles is not possible.

In conclusion, patent DE 43 07 407 C2 discloses a device for producing cigarettes in which the light tobacco particles are separated from the waste material with the heavier tobacco particles. There is no mention of monitoring the quality of separation using a suitable sensor.

SUMMARY OF THE INVENTION

An object of the invention is to provide a method of detecting the mass stream of particles of a winnowings stream in the production of smokable articles, which overcomes the disadvantages of subsequent sieve analysis. In particular, a method is proposed which works online and can thus be employed to optimize the screening conditions as regards product quality and the elimination of winnowings exclusively.

This objective is achieved by the features set forth in claim 1.

Expedient embodiments are defined by the features of the sub-claims.

The advantages achieved by the invention are based on an optical method which functions by using a fine-beam light barrier and detects from the darkening of the light beam of the fine-beam light barrier an average dimension and an average volume of the winnowings particle based statistical considerations.

This measurement furnishes primarily information on the particle size distribution, since the individual particles are measured separately, from which the average dimension, the average volume, the average particle mass and the particle mass stream are continuously determined.

The measured value thus obtained for the mass stream is independent of the transporting velocity of the winnowings stream since the particle velocity is directly measured in the device, for example, by employing a second fine-beam light barrier, and in computing the aforementioned parameters. In this way, the slip of the particles in the stream is also taken into account and the measuring device is self-sufficient, independent of other sensors.

Measuring is achievable without any complicated designs for the input and output of the winnowings stream, simply by transporting the winnowings stream, extracted from the cigarette maker, through a transporting/sensor tube on which the or each fine-beam light barrier is arranged. The necessary overall height required is less than 100 mm so that space should remain available everywhere for installing this sensor.

This optical measuring method results in no additional degradation of the winnowings stream, since the sensor works contact-free, and can be inserted with zero impact and with no change in cross-section directly into an existing transport tube which may directly serve as the sensor tube.

The relatively straightforward configuration of the mechanical/physical part of the sensor ensures high reliability coupled with a relatively low price, especially when buying in bulk.

BRIEF DESCRIPTION OF THE DRAWINGS

The invention will now be explained in more detail by way of example embodiments with reference to the attached schematic drawings in which:

FIG. 6 is a size/velocity diagram with two particle classes.

DETAILED DESCRIPTION OF THE PREFERRED EMBODIMENTS

Figure 1:
FIG. 1 is an illustration of a winnowings specimen.

FIG. 1 illustrates a winnowings specimen directly imaged by being spread on the scanning surface of a copier. The individual winnowings particles are mostly elongated winnowings with transverse dimensions mainly in the range of 0.5 to 2 mm and longitudinal dimensions in the range of 5 mm to 20 mm.

Accordingly, for the following estimates, a winnowings particle dimension of a=2 mm is computed as averaged over the longitudinal and transverse dimension. The reason for this simplification in the subsequent procedure will be detailed later.

As already mentioned above, upon cigarette production in the cigarette maker the incoming tobacco stream is screened so that only sufficiently fine tobacco material is incorporated in the tobacco bundle, while the remaining portion of coarse material—the winnowings—is discharged at an exit of the cigarette maker and is collected centrally by pneumatic transport for further processing.

FIG. 2a illustrates how, during this path, the winnowings are conveyed through the transport tube which simultaneously serves as the sensor tube. Arranged at this sensor tube is a fine-beam light barrier comprising a light source on a side of the sensor tube and comprising a detector on the opposite side of the sensor tube. The sensing beam runs centrally through the cross-section of the tube, its direction being employed in the following as the y direction of a Cartesian coordinates system.

The radius R of the tube is very large compared to the dimensions of the winnowings particles.

The centerline of the sensor tube is utilized as the z axis of the coordinates system. The x axis of the coordinates system then has the direction indicated in FIG. 2a.

The winnowings particles differ in their trajectories (center of gravity coordinates $\{x_i, y_i\}$ in the sensor) as well as in their shapes sizes and angular orientations. Under steady stream conditions, it may be assumed that the trajectories of the winnowings particles are evenly distributed over the cross-section of the tube on a statistical average.

The transverse dimensions of the light beam are selected as small as possible technically, They may then be assumed to be negligibly small as compared to all dimensions of the winnowings particles, so that in the present context the term "fine-beam light barrier" may be employed.

In actual practice, the sensing light beam has, for example, a diameter $D_s$ of 0.1 mm. The corresponding detectors are designed so that their response is sufficiently fast (for example in the range of 100 ns) to precisely determine the dimensions of the particles at the particle velocity (typically 25 m/s).

In the process of detecting the winnowings particles by means of the fine-beam light barrier, the majority of the transported winnowings particles fly past the light barrier and only a minor portion is actually detected. Since the dimensions of the winnowings particles are very much larger than the beam diameter $D_s$, a short term interruption of the light beam is obtained for a known transport velocity v of each particle passing the fine-beam light barrier. For a given velocity of the particle, the duration $\tau_i$ of the interruption is proportional to the "projected" diameter $s_i$ of the particle on the trajectory. This pulse duration is used together with the measured velocity $v_i$ of the particle to compute its diameter $s_i$ and therefrom its volume and mass. From the mass $m_i$, detected for a sufficiently number of particles during the sensing time $T_O$, the whole mass stream results ultimately.

The bigger the particle, the more chance it has of being detected by the fine-beam light barrier, thus, the detection probability of the winnowings particles needs to be taken into account when computing the mass stream from the light barrier signals. This will now be explained with reference to FIGS. 2b and 2c.

FIG. 2b illustrates a winnowings particle moving along the z direction through the sensor and triggering the fine-beam light barrier. The time duration of the generated interruption depends on the x position of the trajectory, i.e. $\tau_i = \tau(x)$, and on the angular orientation of the winnowings particle.

The plot of the function $\tau(x)$ shown in FIG. 2b applies only to the orientation shown. The width al of the range in which $\tau \neq 0$ is the detection range of the winnowings particle at the given orientation.

Figure 2:
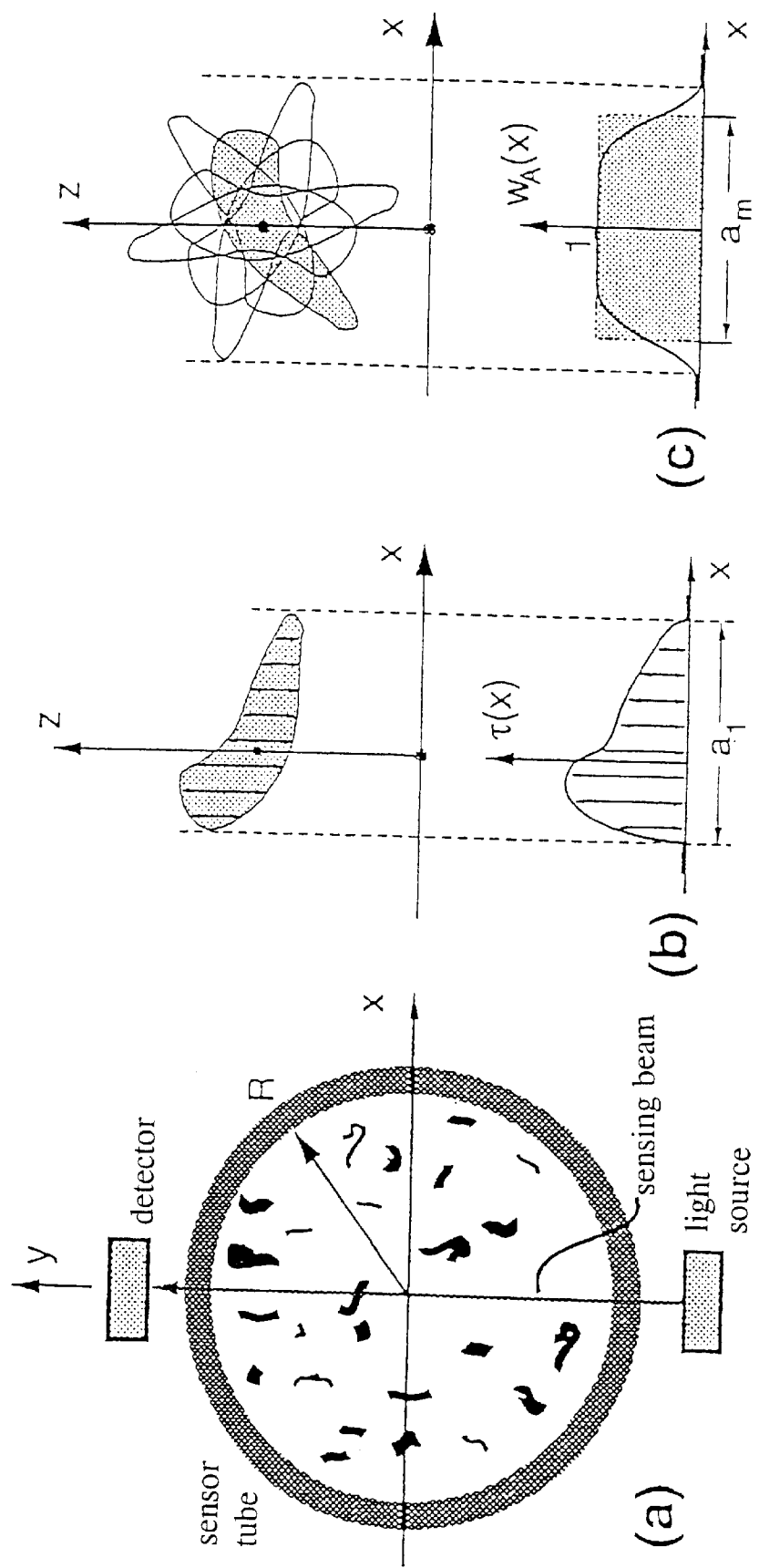
FIG. 2a is a cross-section through the sensor including winnowings particles.
FIG. 2b is a plot of the detection range of a winnowings particle including the given orientation.
FIG. 2c is a plot of the response probability for a winnowings particle of arbitrary orientation.

When now the same winnowings particle is viewed in an arbitrary orientation, then instead of the detection range, a locally-dependent response probability $W_A(x)$ of the light barrier shown in FIG. 2 is represented, this being obtained by averaging over all orientations.

For very small values of |x|, i.e. when the trajectory passes very close to the y axis and thus very close to the light beam, the light barrier reliably responds and there is $$w_A(x)=1.$$

For larger distances |x|, the response probability continuously approaches 0, and thus an average response width $a_m$ is defined in accordance with the equation $$a_m = \int w_A(x)dx$$

In the representation shown in FIG. 2c, this means the width of a rectangle is equal in area to the area under the curve $w_A(x)$. The precise value of this width depends on the shape and size of the particle, but not on its angular orientation, since this has been averaged.

This value $a_m$ permits indication of the probability with which the winnowings particle is counted by the light barrier when its trajectory passes through the cross-section of the sensor tube at some point. This count probability $w_z$ amounts to $$w_z = A_{Pi}/A_Q = a_m \cdot 2R/\pi R^2 = (2/\pi) \cdot a_m/R$$

where $A_{Pi}$ is the area of the strip having the width $a_m$ and the length 2R, in which the winnowings particle is detected, $A_Q = \pi R^2$ indicates the cross-section of the tube.

For a single particle, the response width $a_m$ is proportional to the particle size. Assuming now that the shape spectrum of the particles always remains the same, then the same proportionality applies also for the average values, and an average response width $a_m$ can be given by the equation $$a_m = f_\alpha \cdot \alpha$$

with the average particle size $\alpha$ and a shape factor $f\alpha$ which can be determined empirically (upon calibration of the sensor). Accordingly, with the count probability $w_z$, the average count rate Z can be expressed as $$Z = Nw_z = (2f_\alpha/\pi)N\alpha/R$$

where N is the number of particles streaming through the cross-section of the tube per unit of time.

By means of this equation, the product $N\alpha$ can be determined from the measured count rate Z and be used in computing the mass stream $\mu$, this being $$\mu = Nm_p$$

if $m = f_m\alpha^3$ designates the average mass of a particle. It is proportional to the particle size $\alpha$ to the power of 3. The proportionality factor $f_m$ decisive here must be determined empirically. By combining the above equations, one obtains the mass stream in the formula $$\mu = \frac{\pi}{2}R\frac{f_m}{f_\alpha}Z\alpha^2$$

To further evaluate this expression, the value $\alpha^2$ also needs to be found. It follows from the average duration of the light barrier signal as is shown in the following.

As already explained, the time duration $\tau_i$ of a single light barrier signal depends on the precise position $x_i$ at which the trajectory of the detected particle flies through the plane of the sensor as well as on the size and angular orientation of the particle.

Since the light barrier signal is negligibly thin compared to the winnowings particle dimensions and since the shape spectrum was assumed to be constant, the dependencies of the pulse duration $\tau_i$ on the position $x_i$ and on the angular orientation average out the same for all particles, and the same proportionality of the pulse duration to the size of the particles remains for all particles. Consequently, also the average pulse duration $\tau$ must be proportional to the average particle size $\alpha$ and inversely proportional to the movement velocity v of the particles:

$$\tau = f_t\alpha/v$$

with a shape factor $f_t$ which is characteristic for the present shape spectrum. Thus, in conclusion, one obtains by combining the partial results, as derived above, the formula for evaluating the mass stream $\mu$ $$\mu_1 = \Gamma_1 Zv^2\tau^2$$

wherein all shape factors and other constants of the sensor are grouped together into a single factor $\Gamma_1$. However, due to the numerous assumptions involved in these form factors, computing this factor $\Gamma_1$ does not appear to be expedient. Instead it is ascertained by calibrating the sensor.

Determining the average pulse duration $\tau$ may be done technically by simply adding the time durations $\tau_i$ of all pulses during a sensing time $T_O$ and subsequently to refer the sum to $T_O$. For this purpose, it is sufficient in the simplest case to direct each pulse of a fast quartz-clock to a summing counter during the time in which the light barrier is interrupted ($\tau_i$).

To obtain information about the particle size distribution it is necessary to individually store the time duration $\tau_i$ of each pulse. When upon expiration of the sensing time $T_O$, these values are known for $10^3 \ldots 10^4$ particles, the computer can represent the measured distribution of the $\tau_i$ values graphically on the monitor. In addition, the computer can display the average value $\tau$ and the dispersion width $\Delta\tau$ of the distribution or communicate this by data bus to a higher order process control.

As an alternative to the evaluation described, there is incidentally another method of evaluating the mass stream $\mu$ by computing it from the masses $m_i$ or volumes $V_i$ of all particles flying through the cross-section of the sensor as a whole during a specific sensing time $T_O$:

$$\mu = (1/T_O)\Sigma m_i = (\rho/T_O)\Sigma V_i = (\rho f_v/T_O)\Sigma a_i^3$$

with a shape factor $f_v = V_i/a_i^3$ and $\rho$ is the mass density of the winnowings material. Since not all particles can be detected, this summing is undertaken only with the particles detected by the light barrier. The size-dependent detection probability for each particle is taken into account individually by a weighting factor $g_i$, resulting in $$\mu = (\rho f_v/T_O)\Sigma g_i a_i^3$$

As discussed above, the detection probability is proportional to the size of the particle. This is why it is good practice to undertake the weighting inversely proportional to the size, i.e.

$$g_i = 1/a_i = v/\tau_i$$

After a few intermediate steps, this leads to the following evaluation formula $$\mu_2 = \Gamma_2 Z v^2 \tau_{eff}^2$$

in which $\tau_{eff}^2$ is the root mean square of the light barrier pulse durations and $\Gamma_2$ is another calibration factor to be determined empirically.

Although the equation for $\mu_1$ employs the simple average and the equation for $\mu_2$ the square average, the equations does not contradict one other. Since namely a fixed, constant shape spectrum was supposed, there must also be a fixed interrelation between the two cited average values which must result in corresponding different calibration factors $\Gamma_1/\Gamma_2$. When the aforementioned assumption applies, then it is irrelevant which of the two equations is used for computing the mass stream.

In actual practice, the assumption of the fixed shape spectrum is not satisfied perfectly, however. Then, by comparing the mass stream values determined by the two equations as cited above, it is possible to detect any differences occurring online. If at some point in time, a difference between the computed mass stream values $\mu_1$ and $\mu_2$ is suddenly observed, then evaluating the pulse duration statistic $\tau_i$ may indicate where the cause of the deviation is to be sought and which of the two mass stream values is then of more significance.

From the above considerations, it is thus possible to establish from the pulse durations of the sensing signals of the fine-beam light barrier or from the average pulse duration $\tau$, the average winnowings particle dimension $\alpha$ and other essential parameters of the winnowings particle distribution.

For the above computations, it was necessary to know the movement velocity v of the winnowings particle. Various methods are available for measuring this, in the simplest case, the pneumatic transport velocity in the sensor tube should suffice.

Figure 3:
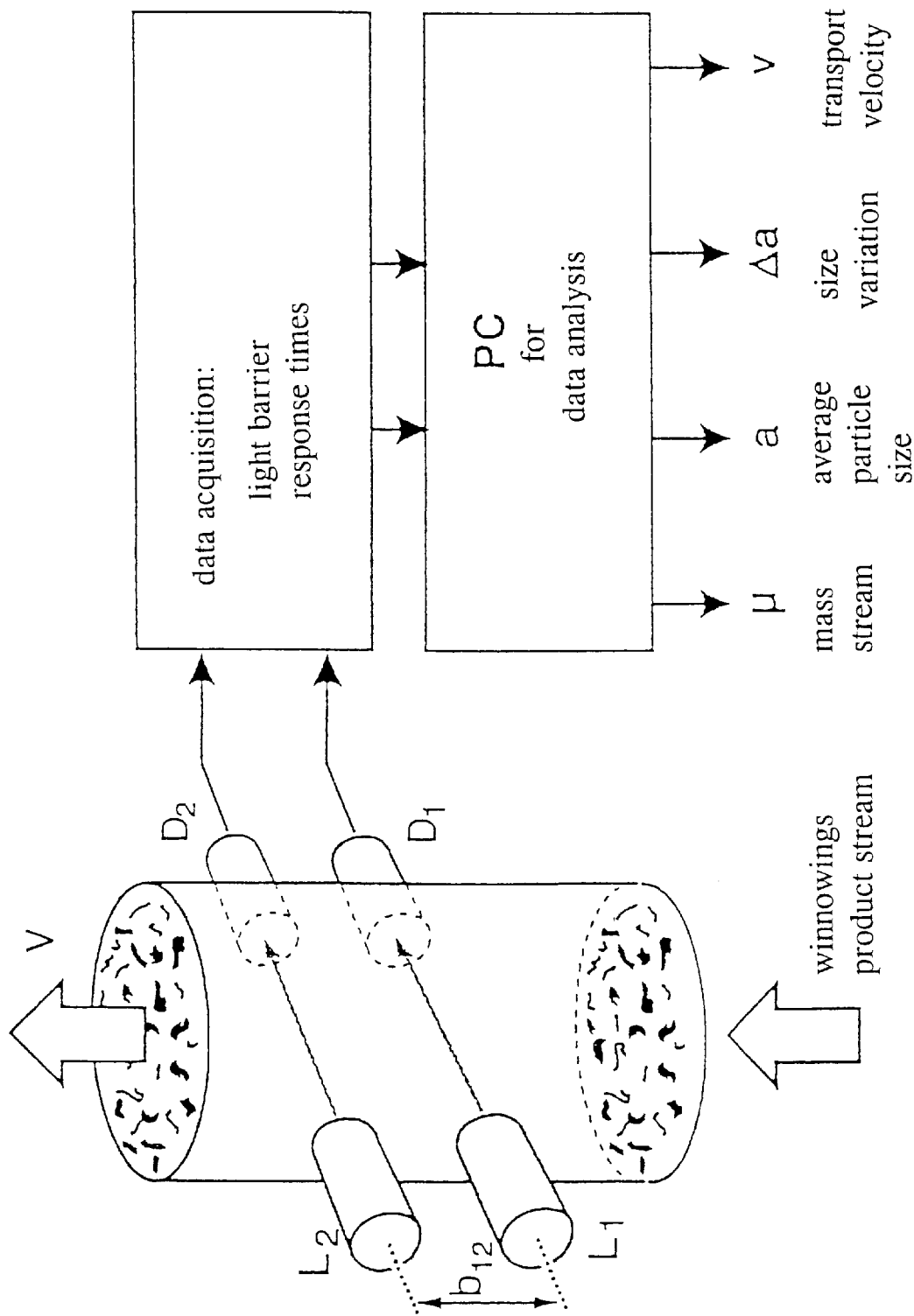
FIG. 3 is a schematic construction of mass stream measuring with two fine-beam light barriers in the winnowings particle stream.

In accordance with a preferred embodiment, the winnowings product stream is scanned with the aid of two fine-beam light barriers, which are located at a short distance $b_{12}$ from each other in series in the sensor tube, see FIG. 3. By evaluating the time difference $t_{12} = v \cdot b_{12}$ of the signals of the 1st and 2nd fine-beam light barriers, it is thus possible to determine the particle velocity v directly in the sensor itself, as a result of which the particle sensor becomes self-sufficing, independent of the other measuring devices.

Such a sensing method incorporating two fine-beam light barriers is able to furnish—in addition to the mass stream $\mu$— the particle size, the size variation and the transport velocity of the winnowings particles, as is evident from FIG. 3.

The two fine-beam light barriers comprise light sources $L_1$ and $L_2$, respectively, as well as detectors $D_1$ and $D_2$, arranged in the sensor tube or outside thereof. When arranged outside of the sensor tube, transparent windows need to be incorporated in the wall of the sensor tube downstream of the light source or upstream of the detectors to permit passage of the fine light beams.

In order to determine the mass stream $\mu$, the light barrier signals of all winnowings particles, which have been observed during a preset sensing time $T_O$, are evaluated. In actual practice, a typical value of this sensing time $T_O$ is $T_O = 100s$. The number of particles detected in this time $T_O$ by the fine-beam light barriers—between 1,000 to 10,000 particles—is sufficiently large to obtain an indication as to the number of winnowings particles transported through the total cross-section of the sensor as a whole with an error in the order of magnitude of 3% or less. By selecting a longer sensing time or by using several fine-beam light barriers arranged in parallel, this accuracy can be further enhanced.

Figure 5:
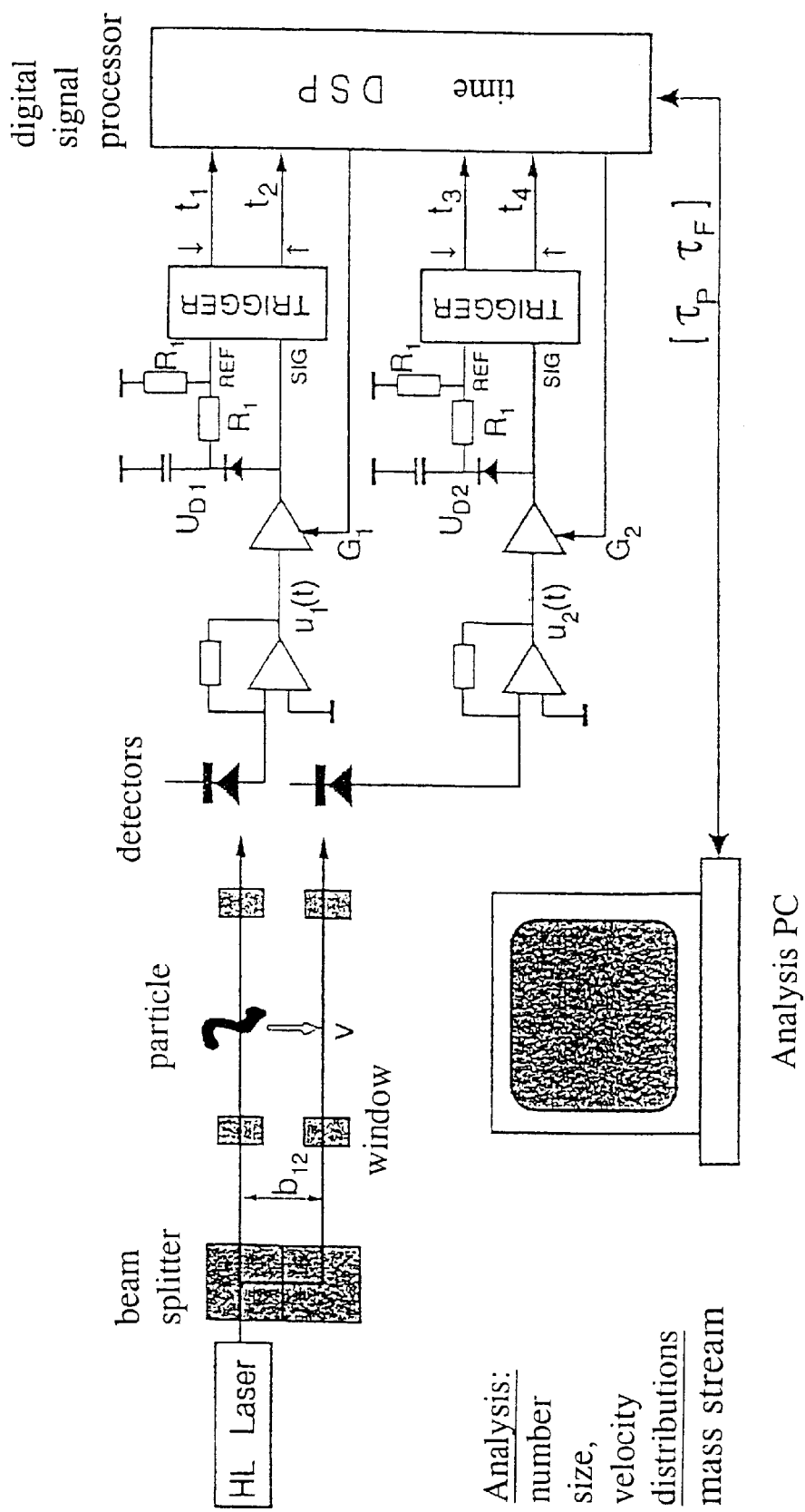
FIG. 5 is a detailed construction of a winnowings mass stream sensor employing two fine-beam light barriers.

The detector electronics circuitry is illustrated schematically in FIG. 5.

Figure 4:
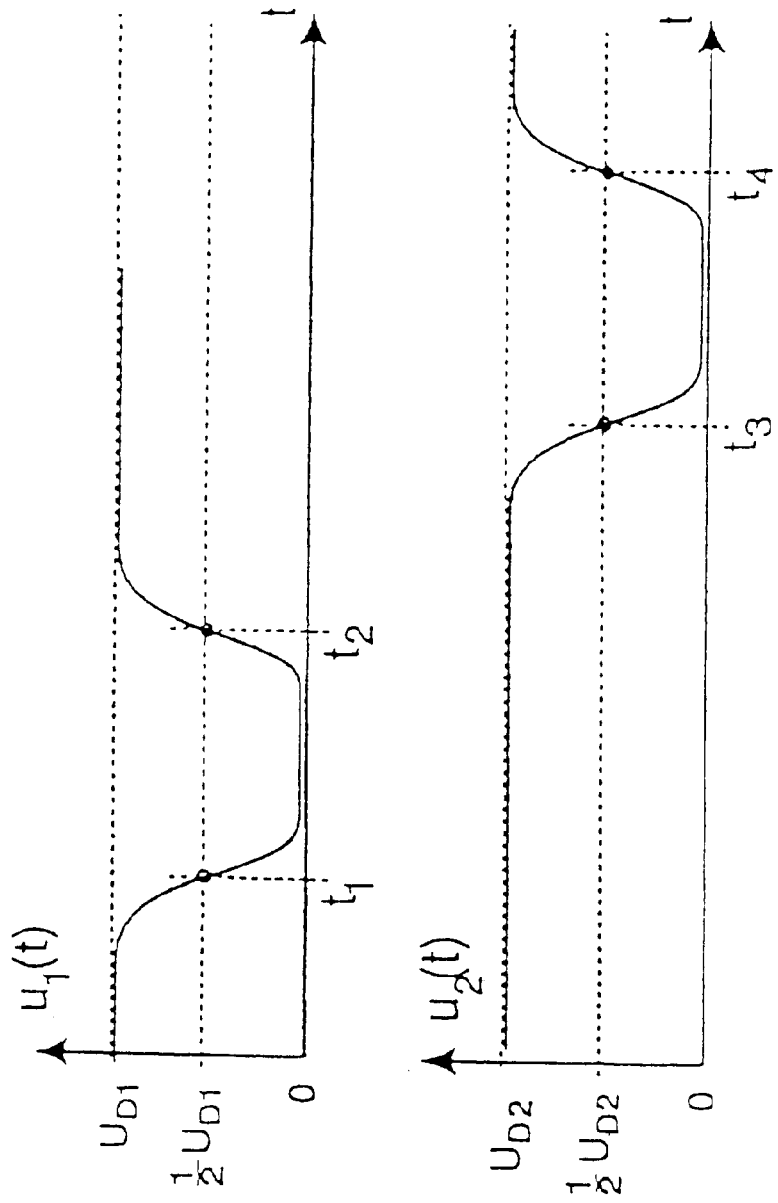
FIG. 4 is a time plot of the output signals of the two fine-bean light barriers.

The concept of the sensor intends that the light beam be totally interrupted by the particles. However, due to stray light and extraneous light, a small signal may still exist even at the dark times. By suitable configuration of the light barriers (long, thin, black tube upstream of the detector), this remnant signal may be rendered so small that an on/off contrast of at least 100:1 is achieved. The result is the signal profile sketched in FIG. 4.

The pulses coming from the detector are "dark pulses". The data to be evaluated from them are the points in time $t_1$ and $t_2$ for the (as viewed in the direction of flight) first light barrier, and $t_3$ and $t_4$ for the second light barrier, as marked in FIG. 4. At these points in time, the voltage $U_1(t)$ or $U_2(t)$ goes through the 50% level of its "normal" value $U_D$ existing during the relatively long pauses between the pulses. In the practical design of the circuit, it is to be noted that the "normal" voltages $U_{D1}$ and $U_{D2}$ at the two light barriers in general slightly differ in level.

Therefore, it is expedient to obtain the voltage levels $U_{D1}$ and $U_{D2}$ from the corresponding detector signals by "peak-type rectification", which bridges the short term "intrusions" (dark pulses) of the voltages $U_1(t)$ and $U_2(t)$, but which adapts to slow changes in the laser power with a time constant of, e.g., 1 s.

From $U_{D1}$ and $U_{D2}$, the voltages $½ U_{D1}$ and $½ U_{D2}$ are obtained in two voltage dividers which serve as reference for the two trigger ICs. These are designed so that normalized output signals TR1 ... TR4 are output when their input voltages $u_1(t)$ and $u_2(t)$ pass through the respective reference voltage from top to bottom (TR1 and TR3) or from bottom to top (TR2 and TR4).

The trigger signals are supplied to digital inputs of a digital signal processor (DSP), each prompting reading of the central clock (e.g. 10 MHz clocking) of the DSP and storage of the momentary time $t_1$. When the last reading ($t_4$) has been made, the data set $[t_1, t_2, t_3, t_4]$ is immediately evaluated in the DSP to determine the average pulse duration $\tau_p$ and the flight time $\tau_F$:

$$\tau_p = (t_2 + t_4 - t_1 - t_3)/2 \quad \tau_F = (t_3 + t_4 - t_1 - t_2)/2$$

Dividing by 2 does not need to be implemented in DSP, this can be done later in the PC evaluation process. This is indicated here, however, to work with more understandable values. Thus, computing $\tau_p$ and $\tau_F$ requires in DSP only additions and subtractions of whole numbers and can be done very quickly, i.e. online.

The data pair ($\tau_p$, $\tau_F$) could then be immediately transferred from the processor to the PC. It is more efficient, however, when a certain number of such data pairs are collected before being transferred, for example 1 per second or every time the DSP internal storage is full. The rate at which these data pairs materialize depends on the mass stream to be measured; practically, it should not exceed 3,000 data pairs/second, although values of up to 10,000 pairs/second are achievable as a limit.

It is not a mandatory requirement to detect every particle prompting the trigger with its data {$\tau_p, \tau_f$f} and to forward it to the PC for evaluation. It is permissible to lock the signal processor from registering further particles during the data transfer to the PC and to re-enable it only after the transfer has been made. This applies with no limitations when these interrupt times constitute only a fraction (less than 1%) of the total time. Since the number of particles to be evaluated statistically in each case is high, the sensing accuracy attained is not substantially reduced by such occasional short interruptions. However, when the 'dead time' of the sensor attains a value greater than approx. 1% of the total sensing time due to the transfers, then it is necessary to list the length of these dead times and to take them into account as a correction factor in the ultimate computation of the mass stream.

In such operations, but also in normal operation, it may happen that the complete set of four time readings [$t_1, t_2, t_3, t_4$] for a particle is not detected. Furthermore, it may happen that two particles are located in the region of the light barriers at the same time, and that their trigger signals chronologically 'mix'. This needs to be checked continuously by the processor, and incomplete data sets [$t_1, t_2, t_3, t_4$] must be barred from being further processed. It is for this purpose that a 'particle time window' is defined for each particle. It begins as soon as a trigger signal TR1 occurs and then covers a fixed predefined (programmable) time duration $T_P$. This time is selected to be somewhat longer than the longest occurring time ($t_4-t_1$) required by the largest particle possible at the slowest transport velocity in being transported through the sensor. The duration of this 'particle time window' is typically in the range $T_P=150-500$ μs. During this time, no further trigger signals TR1 are to be accepted by the processor. To check the completeness of the four time readings required, the three stores for $t_2, t_3, t_4$ could be set to zero on commencement of each time window. Upon arrival of the trigger pulses TR2, TR3 and TR4, these zeros are then overwritten by the read times $t_2, t_3$ or $t_4$. It needs to be assured that writing into each of the three stores only occurs once to avoid confusions which could occur, under circumstances, upon arrival of a subsequent second particle. Upon timeout of the time window $T_P$, a check is made to see whether the three stores $t_2, t_3, t_4$ are really unequal to 0. If so, the data is further processed; if not, the data set is rejected and, at the same time, a counter for registering these operations is elevated by 1. It is not until $T_P$ has timed out that all stores are re-enabled, and a new time window can begin as soon as a new pulse TR1 occurs.

A consequence of introducing this 'particle time window' is that the system is 'dead' during the time $T_P$ and unable to register any new particle which may appear shortly after the first. This results in failure to measure a certain fraction of the particle. An analysis of this situation shows that the probability distribution of the temporal distances of particles following each other is given by an exponential function:

$$w(t)=\exp(-t/T_m)$$

$T_m$ is the average time between two particles. Loss of the signals of particles appearing during the dead time reduces the detection probability of the system from 100% to the value $$D_w=\exp(-T_P/T_m)$$

Since the system knows the average time $T_m$ between the particles, it can compute this reduced detection probability and take it into account as a correction factor in detecting the mass stream. Practically, however, the system as a whole is designed so that this correction generally remains small (<10%).

It is nevertheless good practice to attempt computing $\tau_p$ and $\tau_f$ outside of the time window, where possible, to lose as little sensing time as possible. This is achievable in actual practice, because the DSP has relatively little to do during the time window (except for storing the three times) so that computing $\tau_p$ and $\tau_f$ of a data set can be implemented on each commencement of the following data set.

For the same reason it is good practice to define the length of the time window 'dynamically', i.e. adapted to the transport velocity at any one time. Another step in the same direction is also to split the time window into two such windows, i.e. one for each of the two light barriers, and to temporally stagger these windows by the flight time $\tau_f$. In this way, the dead time occurring as a whole can be roughly halved compared to the situation described above with one single fixed time window covering all points in time $t_1-t_4$.

Should a particle merely "skim" the beam of a light barrier, the dark pulse generated is not fully configured, but only in part. If, in the minimum of the pulse, the signal $u_1(t)$ remains totally above the trigger threshold ½ $U_{D1}$, the corresponding particle is simply ignored. The same applies to the other light barrier. This is not so simple for the case in which the signal, although falling below the trigger threshold ½ $U_{D1}$ and producing a trigger signal TR1, is only slightly below the threshold. For then the corresponding particle is registered as having a pulse duration which is too short, and which does not correspond to its true size.

To reduce the errors resulting from this, the evaluation and transfer of the data set [$t_1, t_2, t_3, t_4$] can be made dependent on the requirement that $u_1(t)$ falls below a second trigger threshold, set for example at 0.1 $U_{D1}$. Accordingly, the signal $u_2(t)$ of the second light barrier would also need checking for total darkening. In actual practice, this error due to only partial darkening is of no significance in measuring the mass stream as long as the particle size spectrum is constant. Depending on the nature of this spectrum, namely a certain fixed fraction of the particles will always escape detection due to these light barrier signals being marked only in part. If the system is calibrated by comparison with a precise offline method (e.g. weighing), then this fraction is already taken into account in the calibration constant. It is only when the spectrum, and thus the cited fraction, change that the calibration would no longer apply and an error would materialize in the mass stream display.

To obtain clean trigger signals, it is good practice to regulate the gain of the preamplifier so that the voltages $U_D$ are approximately constant in value. Should the transmission of the windows diminish in the course of operation, for instance due to dust from the product stream clouding the windows, this regulation is "claimed" more and more. The lower the window transmission, the higher the gain, for which, however, a threshold should be provided at roughly 70% (−3 dB) of the normal value (windows clean). If this threshold is exceeded, the DSP sends an alarm to the PC: "Clean windows!". In this way, self-monitoring of the transmission condition of the windows is achieved.

The functioning principle of the sensor requires the laser beams of the two light barriers to be as slim as possible in the direction of flight so that the particle size can be sensed with good accuracy. This is possible by using a carefully focussed Gaussian beam.

In the direction perpendicular thereto, i.e. transversely to the direction of flight of the particles, there is initially no such restriction on the width 2 $w_{o,q}$ of the laser beams, although here too, it is good practice to make the beam as "slim" as possible. A broad beam namely would have the disadvantage that particles which are smaller in diameter than the width of the beam would no longer totally interrupt the beam, but merely block it in part. These would then be totally neglected in the sensing process due to the second trigger threshold already described in the previous section.

From a formal, mathematical point of view, the two methods described above for computing the mass stream $\mu$ from the sensed interruption times $\tau_i$ of the light barriers can be termed special cases of a more general series of possible methods of calculation, in which the so-called "moments" of the sensed interruption times $\tau_i$ are formed and utilized to calculate the mass stream. For a fixed, given distribution of particle sizes, in principle, each of the time average values formed with q=0,1,2,3 . . .

$$\tau_{[q]} = \left[\frac{1}{N} \sum \tau_i^q\right]^{1/q}$$

can be employed to characterize the mass stream as long as only one matching calibration factor $\Gamma_q$ is used each time. Here, N signifies the number of particles detected during the sensing time $T_O$ so that $Z=N/T_O=1/T_m$ is the average time rate. The average value $\tau_{[q]}$ is formed by averaging over the interruptions times raised to the q-th power. Thus, taking into account the dead time $T_p$ then for each q $$\mu_q = \Gamma_q Z v^2 \tau^2_{[q]} \exp(zT_p)$$

It is evident that the expressions $\mu 1$ and $\mu 2$, resulting from the methods described above, are special cases (for q=1 and q=2) of this more general representation. This is why it is of interest to use several variants of the computing method last formulated above with the three parameter values q=1,2,3 for the mass stream evaluation.

When there is a change in the spectrum of the particle sizes $a_i$, the values of the mass stream $\mu$ computed for various values of q will differ. Establishing the optimal index q is left to practical and detailed testing of the sensor.

It has been assumed in the description hitherto that all particles have the same density p, the same velocity v and the same shape spectrum. If these assumptions are dropped and the velocity $v_i$ is determined individually for each particle, then the particles may differentiate by their densities $p_i$ and by their shapes. The fine-beam light barrier in accordance with the invention can also be used with such sophisticated evaluation technology to classify the particle stream coming from the cigarette maker.

As a rule, the winnowings stream resulting in cigarette production is made up of two components, namely rib particles and leaf or lamina particles. These two components differ both in their density and in their shape; the density of the lamina particles being somewhat higher than the density of the ribs, and the lamina particles having complex shapes while the rib particles are simple and straight in shape.

Due to these differences in the physical properties mentioned, the rib particles, on the one hand, and the lamina particles, on the other, also move at different velocities relative to the carrier stream of the pneumatic tobacco transport.

Since both the individual particle size and the velocity of the particles can be determined by the fine-beam light barrier comprising two laser beams, these two measurement values are displayed in the graphical representation according to FIG. 6, which plots the size of the particles relative to their velocity.

As may be seen, in this plot the measurement values are concentrated in two ranges to which two different classes of particles can be assigned, namely the ribs as particle class 1 and the lamina particles as particle class 2.

The measurement values held in the DSP are restricted to intervals which are assigned the resulting particle classes. When the mass streams are selected only within the intervals of the individual particle classes, then the mass streams can also be determined separately for the individual particle classes, namely lamina particles and rib particles.

The positions of the individual particle classes in the size/velocity plot can be established either by computation using the known stream-mechanics formulae or by calibration using measuring techniques by transporting scans of the individual particle classes available, in particular lamina particles and ribs, through the sensing circuit and obtaining the measurements. The ranges in which the lumped measuring results materialize for the individual particle classes are then assigned to the corresponding particle classes.

In this way, the fine-beam light barrier in accordance with the invention may also be employed as a "rib sensor" or as a "lamina sensor" so that, by using a suitable feedback loop, interventions may be made in the cigarette production process to, for example, reduce the proportion of lamina particles in the winnowings mass stream.

It has turned out to be useful not to base the size/velocity plot on the actual velocities, but on the relative velocity with respect to the velocity of the transport medium for the tobacco particle stream, i.e. the so-called slip velocity $v_s$ according to the equation $$v_s = v_f - v$$

where $v_f$ is the velocity of the fluid transport medium of the tobacco particle stream and v is the velocity of the tobacco particles detected by the two fine-beam light barriers.

The velocity $v_f$ of the fluid transport medium is determined either by a separate sensing device, for example an anemometer, or from the resulting maximum velocities v corresponding to the velocities v of the smallest, still detectable tobacco particle, whose slip is very low and which, thus, represents in good approximation a mass for the velocity $v_f$ of the transport medium.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method of detecting the particles of a tobacco particle stream in the production of smokable articles comprising the following features:

a) scanning the tobacco particle stream by means of a first fine-beam light barrier having a beam diameter ($D_s$), b) which is smaller than the dimensions of the tobacco particles;

c) evaluating an average dimension (a) and an average volume (V) of the tobacco particles from the distribution of the dimensions ($a_i$) of the tobacco particles determined by darkening of the fine-beam light barrier;

d) determining the velocity (v) of the tobacco particles by using a second fine-beam light barrier arranged at a defined spacing ($b_{12}$) away from said first fine-beam light barrier, said velocity computed from the flight time ($t_{12}$) between said two fine-beam light barriers and their known spacing ($b_{12}$);

e) wherein a particle time window is defined for each detected particle in which no further particles are registered.

2. The method as set forth in claim 1, wherein the size of the tobacco particles is computed from the time duration of an individual signal of said first fine-beam light barrier.

3. The method as set forth in claim 1, wherein the average dimension of the particles ($a_{[q]}$) is computed by evaluating the $q^{th}$ moment of the dark times $$\tau_{[q]} = (N^{-1} \Sigma \tau_i^q)^{1/q}$$

where N is the number of particles detected during a predefined sensing time, q is a small whole number and v is the particle velocity: $a_{[q]} = v \tau_{[q]}$.

4. The method as set forth in claim 1, wherein the mass stream ($\mu$) of the tobacco particle stream is computed from the average size of the tobacco particles ($a_{[q]}$) and their velocity (v).

5. The method as set forth in claim 1, wherein the average sizes of the tobacco particles ($a_{[q]}$), computed for the various values of the parameter q, are continuously compared to each other to establish changes in the size distribution of the particles from sudden changes in their ratios.

6. The method as set forth in claim 1, wherein the beam diameter ($D_s$) of said first fine-beam light barrier ranges between 0.01 to 0.2 mm and a first and second detector ($D_1$, $D_2$) of said fine-beam light barriers has a fast response time constant smaller than 100 ns.

7. The method as set forth in claim 1, wherein the trigger voltage for the response of the light barriers is obtained by peak-type rectification and voltage dividing from the light barrier signal itself.

8. The method as set forth in claims 1, wherein the optical transmission between the light source and the photodetector is monitored at the times when the beam is not interrupted by particles, and that an alarm communication is generated upon falling below of a preset value.

9. The method as set forth in claim 8, wherein the gain of the signal of the fine-beam light barrier is regulated so that on a long-term time average a constant predefined voltage value is obtained, and that the voltage regulator signal is used to generate the alarm communication.

10. The method as set forth in claim 1, wherein the tobacco particle stream is transported through a sensor tube which is penetrated by the fine-beam light barrier.

11. The method as set forth in claim 1, wherein the radius (R) of the sensor tube is very much larger than the dimensions of the tobacco particles.

12. The method as set forth in claim 1, wherein the output signals of the fine-beam light barriers are evaluated for all tobacco particles triggering the fine-beam light barriers during a preset sensing time ($T_O$) in order to determine the mass stream ($\mu$) of the tobacco particles.

13. The method as set forth in claim 1, wherein the two fine-beam light barriers are spaced so little away from each other that both furnish signals of the same kind in very good approximation.

14. The method as set forth in claim 1, wherein the average size (a) of the tobacco particles is determined from the average pulse duration ($\tau$) of the or each fine-beam light barrier taking into account a shape factor ($f_i$) characteristic for the shape spectrum of the tobacco particles.

15. The method as set forth in claim 1, wherein the dead time of the sensor ($T_p$) caused by the particle time window, is taken into account correctively in computing the mass stream ($\mu$), that the mass stream computed from the particles detected outside of the particle time window is multiplied by the factor $\exp(T_p/T_m)$, where $T_m$ is the average time spacing of the particles.

16. The method as set forth in claim 1, wherein, in a calibration run, the shape/calibration factors needed for evaluation are determined, which are used in evaluating the measurements results.

17. The method as set forth in claim 1 wherein the tobacco particles are winnowings.

18. The method as set forth in claim 1, wherein, by evaluating the measured velocities ($v_i$) of each particle, its slip velocity ($v_s$) is determined relative to the transport medium, and that from this an assignment of the particle to a particle class characterizing the density and shape is undertaken for the measured particle size ($a_i$).

19. The method as set forth in claim 18, wherein, by classing the measured values in a size/velocity plot, the individual particle classes occurring in the tobacco particle stream, in particular lamina particles and rib particles, are distinguished.

20. A device for detecting the particles of a tobacco particle stream in the production of smokable articles comprising the following features:

a) a sensor, through which the tobacco particle stream is pneumatically transported;

b) a first and a second fine-beam light barrier, provided in the sensor, the diameter of said fine-beam light barriers being smaller than the dimensions of the tobacco particles; and c) an evaluating device for determining an average dimension and an average volume of the tobacco particles from the dimensions ($a_i$) thereof determined by darkening of said fine-beam light barriers;

wherein, at a defined spacing ($b_{12}$) from the first fine-beam light barrier, said second fine beam light barrier is arranged for determining the velocity (v) of the tobacco particles;

wherein an arrangement for determining the velocity of the transport medium for the tobacco particle stream is provided.

21. The device as set forth in claim 20, wherein the arrangement for determining the transport velocity of the tobacco particle stream is an anemometer.

22. The device as set forth in claim 20, wherein the maximum particle velocity assigned to the smallest tobacco particle is used as the value for the velocity of the transport medium for the tobacco particle stream.

* * * * *